United States Patent [19]

Reynolds et al.

[11] Patent Number: 5,299,864

[45] Date of Patent: Apr. 5, 1994

[54] LABORATORY CONTAINER ROLLING DEVICE

[75] Inventors: Cedric S. Reynolds; Donald A. Boschker, both of Greensboro, N.C.

[73] Assignee: Stovall Life Science, Inc., Greensboro, N.C.

[21] Appl. No.: 970,912

[22] Filed: Nov. 3, 1992

Related U.S. Application Data

[63] Continuation of Ser. No. 857,479, Mar. 25, 1992, abandoned.

[51] Int. Cl.⁵ ............................................. B01F 9/02
[52] U.S. Cl. ................................... 366/233; 366/235
[58] Field of Search ..................... 16/257, 259, 265; 193/35 R; 198/780, 410; 99/421.4, 421.44, 441; 366/205, 208, 218–220, 233, 235; 414/433; 422/99; 435/312, 316; 51/164.1; 211/60.1, 69

[56] References Cited

U.S. PATENT DOCUMENTS

| 926,639 | 6/1909 | Burr | 366/235 |
| 1,414,197 | 4/1922 | Maddox | 366/208 |
| 1,445,488 | 2/1923 | Clark | 366/233 |
| 1,655,174 | 1/1928 | White | 16/259 |
| 1,983,164 | 12/1934 | Bush | 366/208 |
| 2,185,979 | 1/1940 | Dumas | 99/441 |
| 2,395,593 | 2/1946 | Trager | 366/208 |
| 2,990,929 | 7/1961 | Attwood | 193/35 R |
| 3,338,795 | 8/1967 | McBee | 366/208 |
| 3,764,112 | 10/1973 | Jelley | 366/233 |
| 4,227,794 | 10/1980 | Tabin | 366/208 |
| 4,307,965 | 12/1981 | Catarious | 366/208 |
| 4,373,029 | 2/1983 | Nees | 366/235 |

FOREIGN PATENT DOCUMENTS

| 142000 | 6/1980 | Denmark | 366/208 |
| 3923132 | 9/1990 | Denmark | 366/208 |
| 1049663 | 1/1952 | France | 99/421 |

*Primary Examiner*—Philip R. Coe
*Assistant Examiner*—Terrence R. Till

[57] ABSTRACT

A laboratory container rolling device is provided which has a relatively low profile for use in confined spaces such as in refrigerators, ovens or other small compartments. Removable rollers allow the device to accommodate various diameter containers and the variable speed feature accommodates precise speed setting. Safeguards are provided to prevent container damage during extended usage to maintain the container properly upon the rollers.

14 Claims, 4 Drawing Sheets

LABORATORY CONTAINER ROLLING DEVICE

This is a continuation of application Ser. No. 07/857,479 filed Mar. 25, 1992, now abandoned.

BACKGROUND OF THE INVENTION

1. Field Of The Invention

The invention herein pertains to container rolling devices and specifically to rolling devices for bottles, test tubes and other containers as are used in laboratories for cell cultures, filter blot applications, hybridization and for other solutions and procedures.

2. Description of The Prior Art And Objectives Of The Invention

Various laboratory stirrers, shakers, and blenders have been available in the past to stir or agitate fragile filter bolts and other sensitive solutions in chemical and biological laboratories. Also, devices which rotate containers for stirring have also been used in prior industrial and laboratory procedures. With the recent advancements in biological techniques a multi-functional container rolling device is required which will perform under many different conditions and provide a variety of options for the technician. For example, a container rolling device for modern biological laboratories must be portable to operate on bench tops or in incubators and refrigerated chambers as needed. The size of the rolling device and particularly its height is of paramount importance since oftentimes incubators and laboratory refrigerators have minimum interior heights. Presently available devices generally do not meet the versatility or precision requirements for modern biological laboratory equipment and techniques and therefore the present invention was conceived with one of its objectives to provide a container rolling device which can be used in a modern laboratory under a large number of conditions and limitations.

It is another objective of the present invention to provide a laboratory rolling device which will securely maintain a plurality of various sized containers thereon for simultaneous rotation.

It is yet another objective of the present invention to provide a container rolling device in which one or more rollers can be easily and conveniently removed for the accommodation of larger vessels.

It is still another objective of the present invention to provide a container rolling device in which the speed of the rotation can be easily and precisely adjusted.

It is still yet another objective of the present invention to provide a laboratory rolling device in which the overall height is relatively low for use in a limited height controlled environment such as in an incubator or refrigerator.

Various other objectives and advantages of the present invention become apparent to those skilled in the art as a more detailed presentation is set forth below.

SUMMARY OF THE INVENTION

The aforesaid and other objectives are realized by a container rolling device for use in laboratories to gently, smoothly and evenly agitate solutions for cell cultures, filter washings, hybridizations and for other techniques and procedures. The invention is of relatively low profile and includes a series of horizontally aligned rollers which are geared to turn in unison and are driven by an electric motor which is precisely controlled by a front mounted external knob. Each roller has a polymeric friction producing outer surface to encourage gripping of the container and each roller is independently removable whereby a variety of roller configurations can be provided to readily accommodate the particular sizes and diameters of the containers used. A housing surrounds the motor and gear drive and includes a front stop or bumper to terminate container forward movement longitudinally of the device. Similarly, a rear frame bumper at the idle end of the rollers terminates rearward movement of the containers during rotation.

DESCRIPTION OF THE PREFERRED EMBODIMENT

Figure 2:
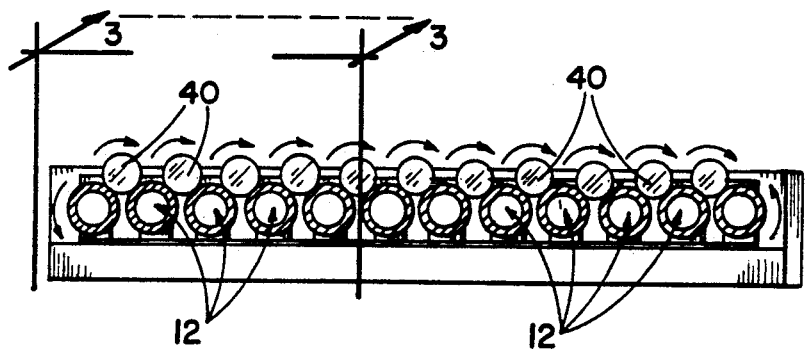
FIG. 2 demonstrates a cut-away view thereof along lines 2—2 of FIG. 1 showing test tubes placed between the rollers for agitation purposes.
Figure 3:
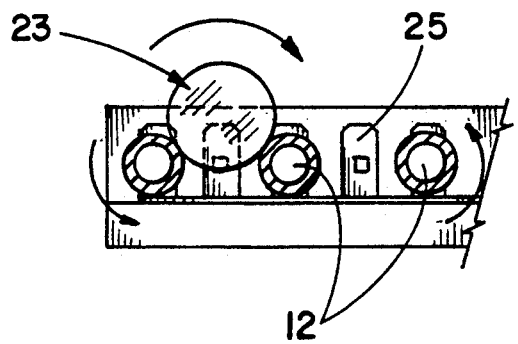
FIG. 3 demonstrates a section of the cut-away view along lines 3—3 of FIG. 2 with a relatively large container thereon.
Figure 4:
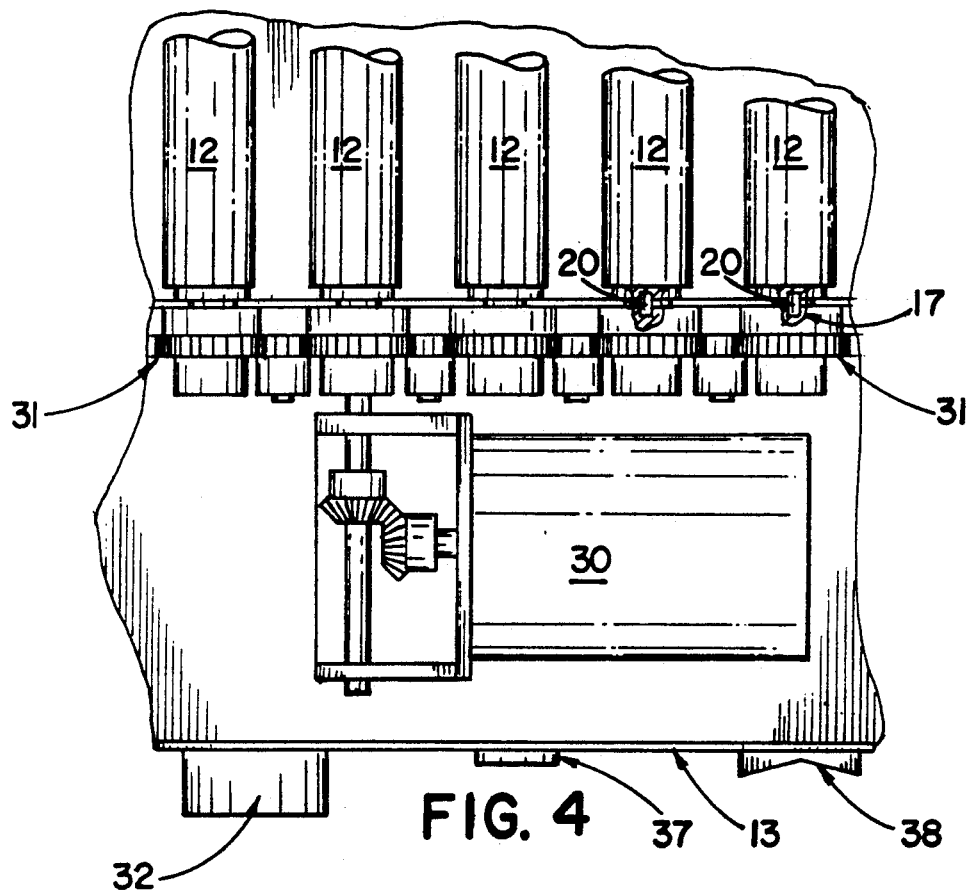
FIG. 4 demonstrates a top plan view of the invention as shown in FIG. 1 with the motor and gear train exposed.
Figure 5:
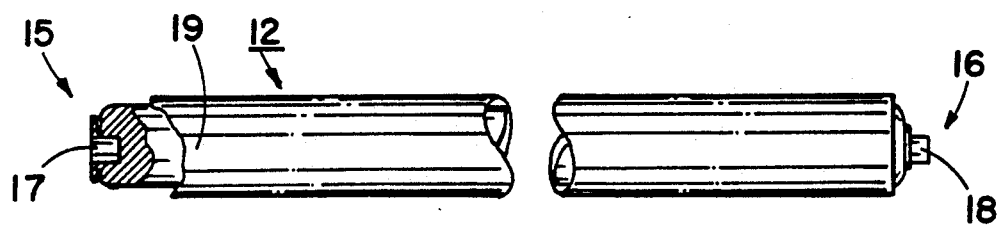
FIG. 5 illustrates an elevational view of one of the rollers having a portion of the outer surface removed.
Figure 6:
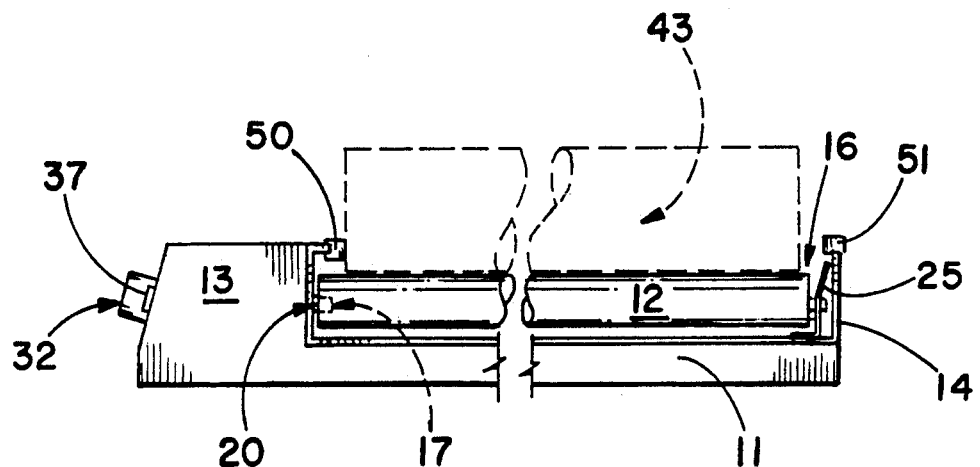
FIG. 6 demonstrates a fragmented side elevational view of the device showing a large container thereon.
Figure 7:
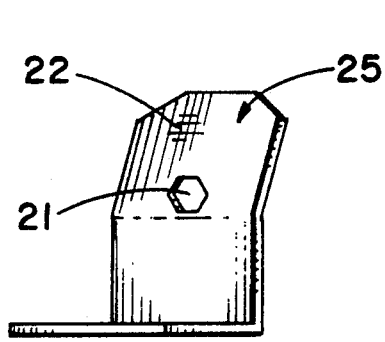
FIG. 7 demonstrates one embodiment of a portion of a roller mount.

The preferred form of the invention is shown in FIGS. 1-4 and FIG. 7 whereby a low profile laboratory container rolling device having a roller height of only two and three-eighths (2⅜) inches and an overall height of only three and three-quarter (3¾) inches, includes a frame upon which eleven (11), one and one-eighths (1⅛) inch diameter parallel horizontally aligned rollers, ten (10) inches in length are mounted. At one end of the rollers a gear train is positioned in a housing and is powered by a variable speed electric motor for turning the rollers in unison at one to thirty (1–30) rpms. One of the rollers of the preferred embodiment is shown in FIG. 5 which includes a drive end for receiving a gear train drive stud and at the opposite (idle) end of the roller, a bearingly supported roller stud projects therefrom. The roller stud is inserted through an aperture of a spring steel roller mount as shown in FIG. 7. The roller mount is resiliently pivotal to accommodate manual release of the roller as desired and is treated with a friction reducing surface, particularly polytetrafluoroethylene to reduce the friction of any container which may contact the roller mount during rotation. The outer surface of the roller is coated with a non-slippery synthetic polymeric substance to frictionally engage a container placed thereon for gentle slow, medium or rapid rotation as required. The electrical motor is a twenty-four volt dc type and as shown in FIG. 4 drives a gear train that provides a positive action simultaneously to each of the rollers and prevents slippage and stalling. In FIG. 6, the preferred embodiment of the device illustrates a pair of nylon bumpers mounted at both the drive and idle ends of the rollers to terminate movement of the containers longitudinally along the axes of the rollers during rotation.

DETAILED DESCRIPTION OF THE DRAWINGS AND OPERATION OF THE INVENTION

Figure 1:
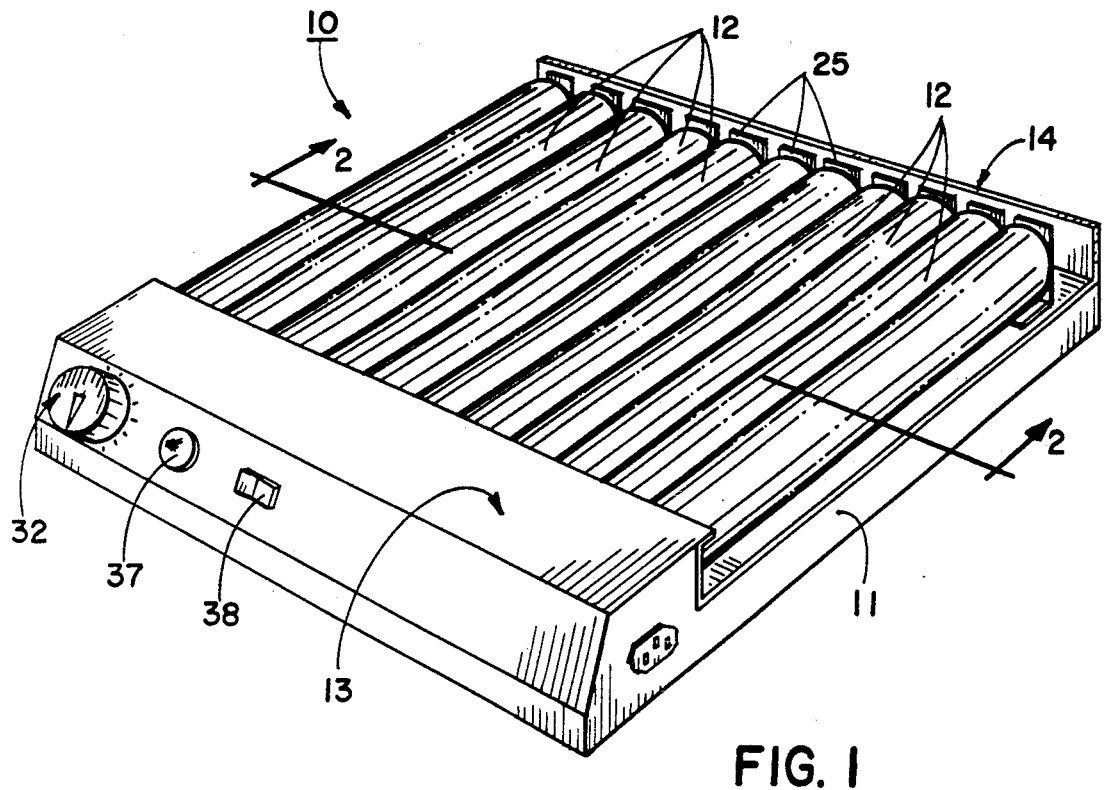
FIG. 1 illustrates a perspective view of the invention.

Turning now to the drawings, for a more complete understanding of the invention and its operation, FIG. 1 illustrates in perspective view laboratory container rolling device 10 having a frame 11 upon which rollers 12 are mounted. Rolling device 10 comprises eleven, one and one-eighth inch diameter rollers which are horizontally aligned and extend rearwardly towards rear wall 14 from drive housing 13. Rollers 12 comprise a drive end 15 and an idle end 16 as shown in FIG. 5. Drive end 15 includes a stud well 17 whereas idle end 16 comprises a protruding roller stud 18 which is bearingly mounted for turning purposes. Roller 12 includes a friction producing surface 19 which may consist of a synthetic rubber or other suitable polymeric covering for contacting and rotating various containers.

Roller 12 is mounted on frame 11 as gear train drive stud 20, which extends from drive housing 13, is positioned within stud well 17. Drive stud 20 may, for example have a hexagonal or square configuration to cooperatively engage stud well 17 which is likewise configured. Roller stud 18 also may have a hexagonal or rectangular cross-sectional configuration to likewise fit within stud aperture 21 of roller mount 25 as seen in FIG. 7. FIG. 7 displays only one roller mount although it would be understood that each roller is attached to a separate roller mount 25 as indicated in FIG. 1. Roller mount 25 consist of a relatively thin but durable spring steel which has been coated with a polytetrafluoroethylene coating 22 to provide a reduced friction surface in the event container 23 as shown in FIG. 3 makes contact therewith. Roller mount 25 has a slightly bent or angular upper configuration as more clearly shown in FIG. 6 to assist in the manual removal of roller 12. Thus, by finger pressure mount 25 which is affixed to frame 11 and which extends above roller 12 can be pivoted rearwardly (towards rear wall 14) to facilitate removal of roller 12 which is accomplished by first lifting idle end 16 upwardly with roller mount 25 in a rearwardly urged posture, and then by sliding stud well 17 from drive stud 20.

Figure 8:
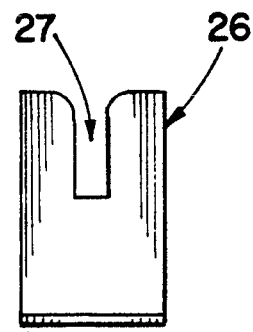
FIG. 8 demonstrates yet another embodiment of a portion of a roller mount.

In an alternate embodiment, roller mount 26 is shown in FIG. 8 which comprises a spring steel member substantially the same size as roller mount 25 but instead of an aperture, contains roller stud slot 27. As with roller mount 25, mount 26 also includes a polytetrafluoroethylene coating to reduce friction if contacted by container 23 of FIG. 3 which may "walk" rearward during rotation. Roller stud 18 can be easily slid into and from roller mount 26.

To increase the versatility of rolling device 10, the overall outside height may be only for example, two and one-half to three and one-half times the diameter of roller 12. It has been found that a suitable diameter of roller 12 is one and one-eighths inches with a length of ten inches. The overall length and width of rolling device 10 therefore may be for example, fourteen and one-quarter inches wide by fifteen inches long. These relatively small dimensions allow device 10 to be used in a small refrigerated environment or in an incubator or oven having temperature ranges from 0°–65° C.

The size mentioned above was chosen to accommodate a maximum of three cell culture roller bottles (1850 square centimeters internal surface area). A smaller device could be made to accommodate only one or two roller bottles and the orientation of the rollers would be at ninety degrees from the present orientation. The rollers could be lengthened to accommodate longer bottles and/or additional rollers could be added for special uses resulting in a device with a larger space with a similar relatively low height.

Figure 9:
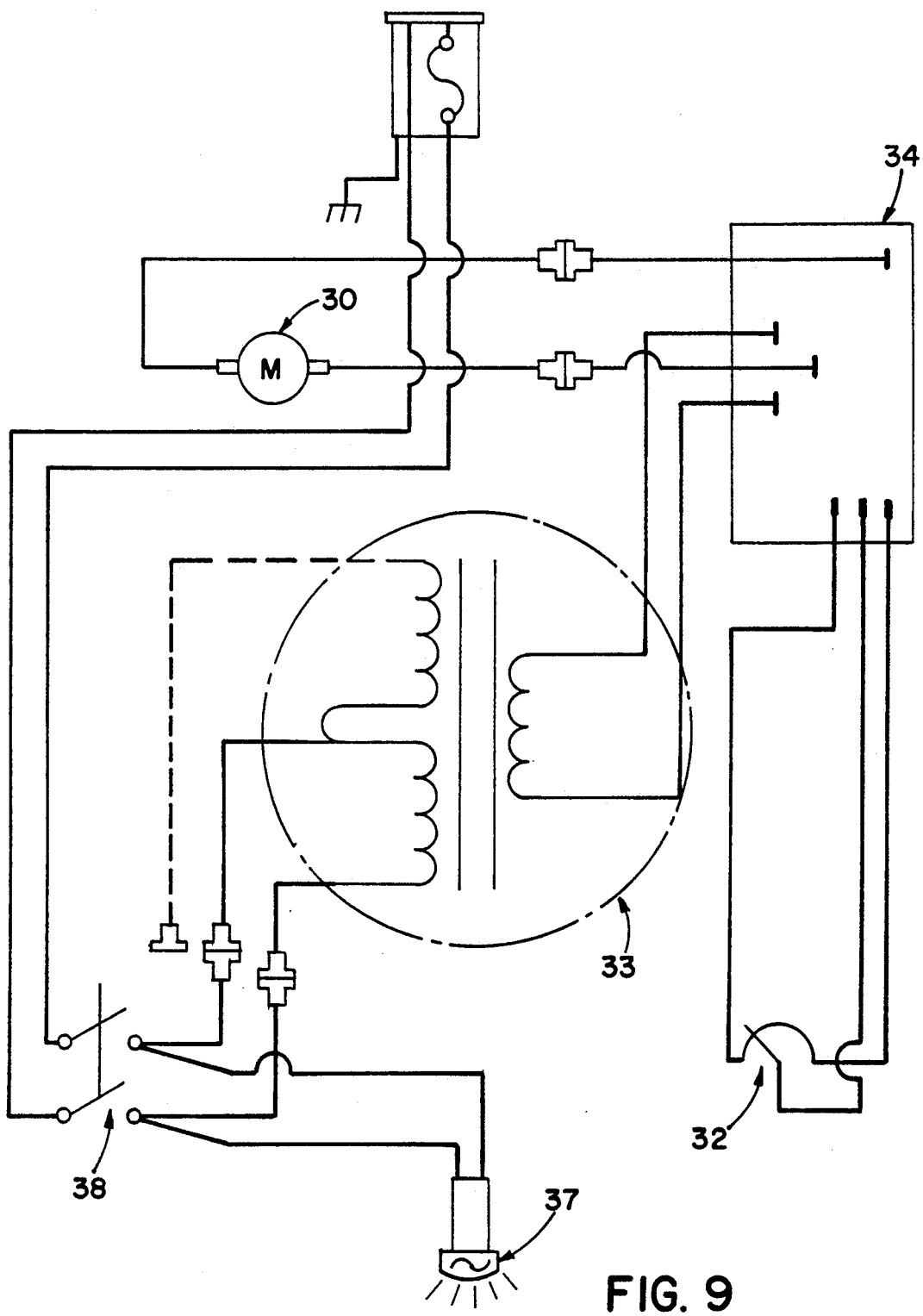
FIG. 9 demonstrates an electrical schematic of the invention.

In order to provide the desired rotational speeds for various vessels and procedures utilized, variable speed dc electric motor 30 is joined to gear train 31 which comprises a series of conventional interconnected gears whereby all rollers 12 are driven at the same speed. Pivotal speed control switch 31 extends forwardly from housing 13 as a convenience to the operator and in FIG. 9 an electrical schematic view is shown whereby transformer 33 is connected to speed control 34 which regulates the rotational speed of dc motor 30. Motor 30 as seen in FIG. 4 is connected to gear drive 31 and indicator light 37 determines whether power switch 38 is on or off as conventional in the art.

As mentioned above, rolling device 10 can accommodate various size solution or other cylindrical containers, and as shown in FIG. 3, alternate rollers are removed to accommodate a relatively large container 23 whereas in FIG. 2, test tubes 40 are being rotated with all rollers 12 in place. Test tube 40 may only have an outside diameter of approximately one to three-quarters of an inch whereas container 23 may have an outside diameter of approximately four and one-half inches or larger and therefore requires a different roller set-up. By turning on power switch 38, power indication light 37 is activated and speed control knob 32 can then be pivoted to adjust the speed of rollers 12 from one to thirty rpms. Power switch 38 is turned off to terminate roller 12 rotation.

As most containers used in biological laboratories are rotated for extended periods, they tend to move along the longitudinal axes of rollers 12 i.e., "walk", and to prevent damage or scraping of the containers, front bumper 50 is affixed to housing 13 and rear bumper 51 is affixed to rear wall 14 as shown in FIG. 6. Bumpers 50 and 51 may be formed from nylon or other materials to prevent damage of container 43 which may for example hold an expensive cell culture or other rare material requiring rotation for ten or more hours within a small, environmentally controlled space.

The illustrations and examples provided herein are for explanatory purposes and are not intended to limit the scope of the appended claims.

We claim:

1. A device for rolling containers comprising: a frame, a plurality of removable horizontally aligned rollers for supporting a container, said rollers each having a drive end and an idle end, a means to drive said rollers, said drive means mounted on said frame, each of said drive ends connected to said drive means, a means to mount said idle roller ends, each of said idle ends engaging said mounting means, said mounting means extending above said engaged rollers, said mounting means comprising individual resilient members having a friction reducing surface, said friction reducing surface to assist container rotation in the event of contact therewith, said mounting means being manually bendable, and each of said resilient members having a roller axle aperture.

2. A device for rolling containers as claimed in claim 1 wherein said drive means comprises an electric motor.

3. A device for rolling containers as claimed in claim 1 wherein said drive means comprises a gear train.

4. A device for rolling containers as claimed in claim 1 wherein said frame comprises a drive housing.

5. A device for rolling containers as claimed in claim 1 wherein each of said rollers comprises a friction producing surface.

6. A device for rolling containers as claimed in claim 1 wherein said idle end of each of said rollers comprises a bearing.

7. A device for rolling containers as claimed in claim 1 wherein said roller mount comprises a pivotal spring steel member.

8. A device for rolling containers as claimed in claim 1 wherein said friction reducing surface comprises a synthetic polymer.

9. A device for rolling containers as claimed in claim 8 wherein said polymer comprises polytetrafluoroethylene.

10. A low profile device for rolling containers comprising: a frame, a drive housing, said housing attached to said frame, a plurality of horizontally aligned independently removable rollers, each of said rollers having a drive end and an idle end, said drive end defining a drive stud well, said rollers mounted on said frame, a means to drive said rollers, said drive means comprising a plurality of drive studs for insertion into said stud wells, said drive means contained within said housing with said drive studs extending therefrom, a plurality of individual pivotal roller mounts, each of said mounts positioned on said frame for receiving a roller idle end, each of said roller mounts comprising a friction reducing surface said friction reducing surface to assist container rotation in the event of contact therewith, said mounts having a roller axle aperture, and said roller mounts extending above said rollers mounted therein.

11. A low profile device for rolling containers as claimed in claim 10 wherein said roller mounts each comprise an angular upper configuration to allow said rollers to be easily manually removed from said mounts.

12. A low profile device for rolling containers as claimed in claim 11 wherein said electric motor comprises a variable speed electric motor.

13. A low profile device for rolling containers as claimed in claim 10 and including a first container bumper, said bumper attached to said housing.

14. A low profile device for rolling containers as claimed in claim 10 and including a second container bumper, said bumper attached to said frame rearwardly of said rollers.

* * * * *